(12) United States Patent
Pottier et al.

(10) Patent No.: US 9,956,175 B2
(45) Date of Patent: May 1, 2018

(54) NANOPARTICLES DELIVERY SYSTEMS, PREPARATION AND USES THEREOF

(75) Inventors: Agnès Pottier, Paris (FR); Laurent Levy, Paris (FR); Marie-Edith Meyre, Paris (FR); Matthieu Germain, Champigny sur Marne (FR)

(73) Assignee: NANOBIOTIX, Paris (FR)

( * ) Notice: Subject to any disclaimer, the term of this patent is extended or adjusted under 35 U.S.C. 154(b) by 1113 days.

(21) Appl. No.: 13/981,757

(22) PCT Filed: Jan. 31, 2012

(86) PCT No.: PCT/EP2012/051507
§ 371 (c)(1),
(2), (4) Date: Nov. 12, 2013

(87) PCT Pub. No.: WO2012/104275
PCT Pub. Date: Aug. 9, 2012

(65) Prior Publication Data
US 2014/0056813 A1   Feb. 27, 2014

Related U.S. Application Data

(60) Provisional application No. 61/437,817, filed on Jan. 31, 2011.

(30) Foreign Application Priority Data

Jan. 31, 2011 (EP) .................... 11305096

(51) Int. Cl.
| | | |
|---|---|---|
| A61K 9/127 | (2006.01) | |
| A61K 41/00 | (2006.01) | |
| A61K 49/18 | (2006.01) | |
| A61K 49/00 | (2006.01) | |
| A61K 9/51  | (2006.01) | |

(52) U.S. Cl.
CPC ........ *A61K 9/1271* (2013.01); *A61K 41/0028* (2013.01); *A61K 49/0002* (2013.01); *A61K 49/1812* (2013.01); *A61K 9/5115* (2013.01)

(58) Field of Classification Search
CPC .................................................. A61K 9/127
See application file for complete search history.

(56) References Cited

U.S. PATENT DOCUMENTS

| | | | | |
|---|---|---|---|---|
| 4,672,040 A | * | 6/1987 | Josephson .......... | B01D 15/1807 252/62.51 R |
| 5,225,212 A | * | 7/1993 | Martin ............. | A61K 47/48815 424/426 |
| 6,726,925 B1 | * | 4/2004 | Needham ............. | A61K 9/127 424/1.21 |
| 2007/0197904 A1 | | 8/2007 | Vigliantietal. | |
| 2009/0004258 A1 | | 1/2009 | Yang et al. | |
| 2014/0056813 A1 | | 2/2014 | Pottier et al. | |
| 2014/0227343 A1 | | 8/2014 | Pottier et al. | |

FOREIGN PATENT DOCUMENTS

| | | |
|---|---|---|
| EP | 2067485 | 6/2009 |
| WO | WO 1993/26019 | 12/1993 |
| WO | WO 2008/033031 | 3/2008 |
| WO | WO 2008/035985 | 3/2008 |
| WO | WO 2012/104277 | 8/2012 |

OTHER PUBLICATIONS

McCarthy et al. (2008). "Multifunctional magnetic nanoparticles for targeted imaging and therapy6." *Advanced Drug Delivery Reviews*, 60: 1241-1251.*
Radu et al. (2015). "Exposure to Iron Oxide Nanoparticles Coated with Phospholipid-Based Polymeric Micelles Induces Biochemical and Histopathological Pulmonary Changes in Mice." *Int. J. Mol. Sci.*, 16:29417-29435.*
Aime, S. et al. "Gd-Loaded Liposomes as $T_1$, Susceptibility, and CEST Agents, All in One" *Journal of the American Chemical Society*, 2007, pp. 2430-2431, vol. 129, No. 9.
Arruebo, M. et al. "Magnetic nanoparticles for drug delivery" *Nano Today*, Jun. 2007, pp. 22-32, vol. 2, No. 3.
Written Opinion in International Application No. PCT/EP2012/051510, dated Aug. 30, 2012, pp. 1-8.
Mahmoudi, M. et al. "Superparamagnetic iron oxide nanoparticles (SPIONs): Development, surface modification and applications in chemotherapy" *Advanced Drug Delivery Reviews*, 2011, pp. 24-46, vol. 63.
Bakandritsos, A. et al. "Synthesis and Characterization of Iron Oxide Nanoparticles Encapsulated in Lipid Membranes" *Journal of Biomedical Nanotechnology*, 2008, pp. 313-318, vol. 4.
Fortin-Ripoche, J.-P. et al. "Magnetic Targeting of Magnetoliposomes to Solid Tumors with MR Imaging Monitoring in Mice: Feasibility" *Radiology*, May 2006, pp. 415-424, vol. 239, No. 2.
Written Opinion in International Application No. PCT/EP2012/051507, dated Sep. 11, 2012, pp. 1-7.

(Continued)

*Primary Examiner* — Brian Gulledge
(74) *Attorney, Agent, or Firm* — Saliwanchik, Lloyd & Eisenschenk

(57) ABSTRACT

The invention pertains to thermosensitive liposomes encapsulating nanoparticles. In certain embodiments, the thermosensitive liposomes of the invention disrupt when heated at gel-to-liquid crystalline phase transition temperature (Tm) or above Tm, wherein the liposome comprises a thermosensitive lipidic membrane encapsulating nanoparticles. The nanoparticles used in the invention comprise an inorganic core the largest dimension of which is less than about 100 nm that is fully coated with an agent responsible for the presence of an electrostatic charge below −20 mV or above +20 mV at the surface of the nanoparticle, the electrostatic charge being determined by zeta potential measurements in an aqueous medium between pH 6 and 8, for a concentration of nanoparticles in suspension in the aqueous medium varying between 0.2 and 8 g/L. The invention also relates to pharmaceutical and diagnostic compositions comprising the thermosensitive liposomes as well as to their uses.

17 Claims, 7 Drawing Sheets

(56) References Cited

OTHER PUBLICATIONS

Golovko, D. et al. "Accelerated stem cell labeling with ferucarbotran and protamine" *European Journal of Radiology*, 2010, pp. 640-648, vol. 20.
Sun, Y. et al. "An improved way to prepare superparamagnetic magnetite-silica core-shell nanoparticles for possible biological application" *Journal of Magnetism and Magnetic Materials*, 2005, pp. 65-70, vol. 285.
Database EMBASE Accession No. 0018572655, Hodenius, M.A.J. et al. "Synthesis, physicochemical characterization and MR relaxometry of aqueous ferrofluids" *Journal of Nanoscience and Nanotechnology*, May 2008, p. 1.
Honda, H. et al. "Study of hyperthermia for cancer using a magnetic liposome particles" *Banyu Life Science Foundation International Drug Discovery Engineering Symposium*, 2005, pp. 29-33, vol. 5.
Toagosei Group, Research Annual Report, Jan. 1, 2011, pp. 27-30, vol. 14.
Zhao, B. et al. "Nanotoxicity comparison of four amphiphilic polymeric micelles with similar hydrophilic or hydrophobic structure" *Particle and Fibre Toxicology*, 2013, pp. 1-16, vol. 10, No. 47.
Gao, Z. et al. "Diacyllipid-Polymer Micelles as Nanocarriers for Poorly Soluble Anticancer Drugs" *Nano Letters*, 2002, pp. 979-982, vol. 2, No. 9.
Cinteza, L. O. et al. "Diacyllipid Micelle-Based Nanocarrier for Magnetically Guided Delivery of Drugs in Photodynamic Therapy" *Molecular Pharmaceutics*, Feb. 14, 2006, pp. 415-423, vol. 3, No. 4.
Andreas, K. et al. "Highly efficient magnetic stem cell labeling with citrate-coated superparamagnetic iron oxide nanoparticles for MRI tracking" *Biomaterials*, 2012, pp. 4515-4525, vol. 33.

* cited by examiner

A

B

A scale bar: 0.2μm

B scale bar: 0.2μm

C scale bar: 0.1μm

D scale bar: 0.1μm

E scale bar: 0.1μm

F scale bar: 0.2μm

G scale bar: 0.2μm

NANOPARTICLES DELIVERY SYSTEMS, PREPARATION AND USES THEREOF

CROSS-REFERENCE TO RELATED APPLICATIONS

This application is the U.S. national stage application of International Patent Application No. PCT/EP2012/051507, filed Jan. 31, 2012, which claims the benefit of U.S. Provisional Patent Application No. 61/437,817, filed Jan. 31, 2011.

FIELD OF THE INVENTION

The present application relates to nanoparticles delivery systems allowing their controlled release, in particular thermosensitive liposomes disrupting at Tm (gel-to-liquid crystalline phase transition temperature) or above Tm, which can be used in the health sector, in particular in human health.

The thermosensitive liposomes of the invention comprise a thermosensitive lipidic membrane encapsulating nanoparticles the electrostatic surface charge of which is advantageously below −20 mV or above +20 mV when measured in an aqueous medium at physiological pH. The encapsulated nanoparticles can be used as a therapeutic or diagnostic agent.

The invention also relates to pharmaceutical and diagnostic compositions comprising nanoparticles delivery systems as defined previously, as well as their uses.

BACKGROUND

A limitation of traditional medical treatment using therapeutic or diagnostic agents is the lack of specificity. Indeed, in most cases, only a small fraction of the administered dose of therapeutic or diagnostic agent reaches the site of interest, while the rest of the agent is distributed throughout the body. This unavoidable distribution into healthy organs and tissue limits the agent's amount that can be administered to a patient, and in turn prevents the agent from achieving the therapeutic or diagnostic effect it is capable of.

The need for site-specific agent delivery vehicles that would not only increase the amount of agent reaching the intended site but would also decrease the amount being delivered to other, healthy parts of the body has been recognized for a long time, in particular for toxic chemotherapeutic drugs. Such vehicles capable of reducing or even eliminating side effects would make the treatment considerably less toxic and more effective. Liposomes have a decade-long clinical presence as nanoscale delivery vehicles for therapeutic and diagnostic agents.

The biggest challenge facing any agent delivery vehicle is to allow the complete release of the encapsulated agents from the vehicle specifically at the diseased site and at a controllable rate.

Moreover, the use of liposomes as delivery vehicles for nanoparticles is still in the preclinical development stages, in particular in the context of externally activable nanoparticles (Al-Jamal, W. T. et al., Nanomedicine, 2007, 2:85-98).

The preparation of liposomes formulated with PEG-lipids containing either a fusogenic or a pH-sensitive lipid to promote destabilization of endosomal membranes and favor quantum dots (QD) cytoplasmic release has been described in vitro (Sigot et al., Bioconjugate Chem. 2010, 21:1465-1472). PEG-lipid dissociation from the liposome can be facilitated by incorporating fusogenic PEG-lipids with a short acyl chain promoting transfer from the liposome to the bilayer within minutes. Alternatively, PEG-lipids can be intracellularly released by adding a cleavable, pH-sensitive PEG analogue in which the polymer moiety is cleaved from the liposome surface upon exposure to the acidic environment of certain endosomal compartments. While such "spontaneous" release can be advantageous (especially for the treatment of distant metastases), since it relies solely on the local environment, liposome content release can still be slow and may not occur at all if the environment is not optimal. The precise control of the liposome's content release is therefore not possible with such liposomes.

The preparation of liposomes comprising a photosensitizer has further been described (US 2010/0233224). The photosensitizer is capable of oxidizing the unsaturated phospholipids of the liposome's membrane when exposed to light and oxygen through peroxidation of lipid chains. Photo-oxidation of liposomes can be triggered to release their load on demand and rapidly through an external light stimulus. The oxidation is responsible for the liposome's membrane failure and for the subsequent release of the liposome's content. However, such a light source can only be used where the targeted tissue is superficially accessible. Liposomes incorporated into deeper tissues cannot be stimulated by light. Liposomes comprising a photosensitizer can therefore not be used to deliver nanoparticles to deep organs or structures of the human body.

Laser activable hollow metal nanostructures have also been used in the past as a means to trigger the permeabilization of the liposome's membrane into which they were encapsulated in order to allow the selective release of a drug (WO 2009/097480).

US 2009004258 describes thermosensitive liposomes encapsulating paramagnetic iron oxide nanoparticles and drugs, the paramagnetic iron oxide nanoparticles allowing the specific or selective release of drugs in a targeted environment under activation by an alternative magnetic field. These liposomes however are not permeable to the encapsulated nanoparticles.

The inventors now herein provide advantageous systems allowing the safe in vivo delivery, and controlled and efficient release, of nanoparticles in a subject.

These systems in particular allow the delivery and release of externally activable nanoparticles in deep structures of the human body. Examples of efficient activable nanoparticles, usable as diagnostic and/or therapeutic tools, were described by the inventors in WO2007/118884, WO 2009/147214 and WO2011/003999.

SUMMARY OF THE INVENTION

The inventors herein provide a thermosensitive liposome disrupting at Tm or above Tm, wherein the liposome comprises a thermosensitive lipidic membrane encapsulating nanoparticles, the "electrostatic surface charge" (also herein identified as "charge" or "surface charge") of the nanoparticles being below −20 mV or above +20 mV when measured in an aqueous medium at physiological pH (between 6 and 8), and the nanoparticles being usable as a therapeutic or diagnostic agent.

The inventors further herein provide therapeutic and diagnostic compositions comprising a thermosensitive liposome according to the present invention and a pharmaceutically acceptable carrier.

In another aspect, the present disclosure provides kits comprising any one or more of the herein-described products, i.e., thermosensitive liposomes and compositions, together with a labeling notice providing instructions for using the product(s).

The thermosensitive liposomes according to the present invention are advantageously capable of protecting nanoparticles from their biological environment and in particular from a premature capture or opsonization by the mononuclear phagocyte system, also herein identified as the reticuloendothelial system (RES).

The liposomes according to the present invention therefore allow the delivery and release of intact nanoparticles upon thermal activation (thermal activation may be reached via a temperature physiological increase or through external activation using, for example, ionizing radiation or High Intensity Focused Ultrasound). Once released on the desired site, the nanoparticles may function as a therapeutic or diagnostic agent, optionally through external activation, as will be further explained below.

The herein-described thermosensitive liposomes are further advantageously capable of delivering nanoparticles to desired sites, in particular to deep sites or structures, of the subject's body through the vascular route.

A precise and efficient control of the nanoparticles' release is (in addition to delivery) now also possible. The release of nanoparticles from the herein-described thermosensitive liposomes has been demonstrated by the inventors for a temperature Tr equal to Tm or above Tm. Interactions between nanoparticles and the lipidic bilayer, responsible for the liposome membrane disruption (membrane physical breackdown, rupture or failure), could explain this surprising result (see FIG. 4E, black arrow).

BRIEF DESCRIPTION OF THE DRAWINGS

FIG. 1 shows the phospholipid molecule structured around the glycerol backbone, sn-1 and sn-2 chains being substituted on the acyl group by long hydrocarbon chains (R1 and R2, comprising at least 9 carbon atoms), and sn-3 chain comprising a polar head with a choline group (N(CH$_3$)$_3^+$) and a phosphate group (PO$_4^-$), conferring a zwitterionic character to the molecule.

FIG. 2A shows TEM observations of 5 nm-sized iron oxide nanoparticles (see example 1) (scale bar=200 nm).

FIG. 2B shows TEM observations of 30 nm-sized iron oxide nanoparticles (see example 2) (scale bar=200 nm).

FIG. 3 shows elution profile for iron oxide-containing liposomes determined by quantification of magnetic nanoparticles by UV-visible spectroscopy (Cary 100 Varian spectrometer) via colorimetric reaction between ferrous ions and phenanthroline. Liposome-containing fractions are collected. The concentration of iron oxide in liposomes ranges from 1 to 2.5 g/L.

Arrow 1 shows the limitation of the cryo-TEM grid holes.
Arrows 2 and 3 respectively shows the liposome membrane and the iron oxide nanoparticles.

Figure 4:
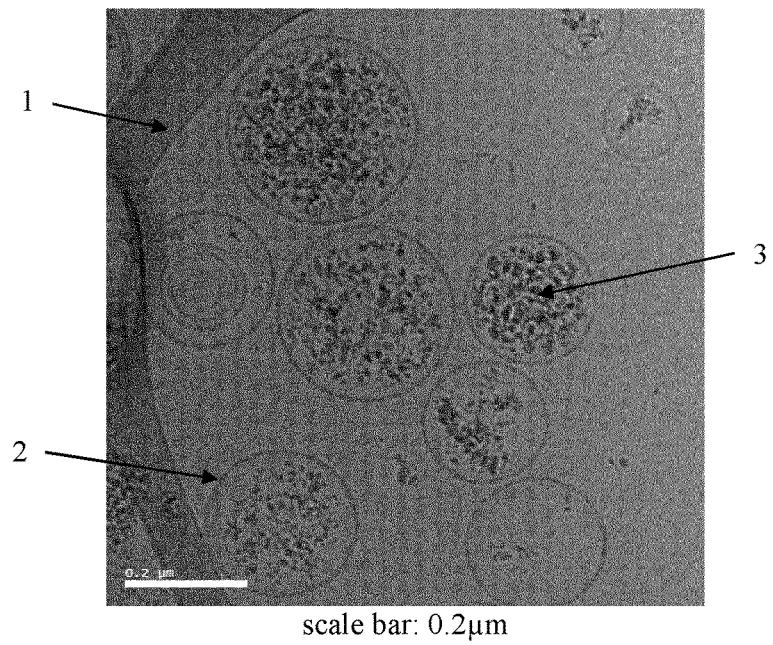
FIG. 4: Cryo-TEM observations of nanoparticle-containing liposomes.
Figure 4:
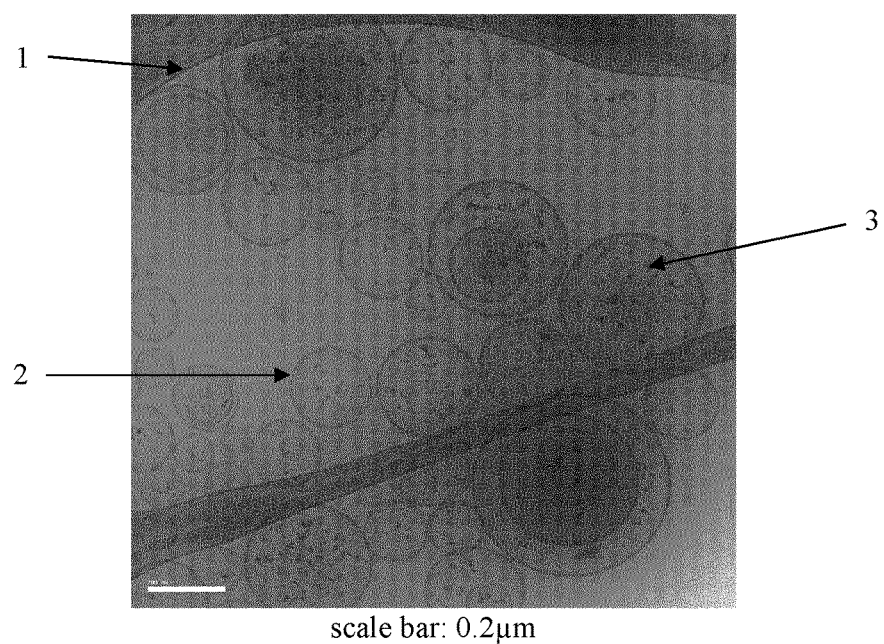
Figure 4:
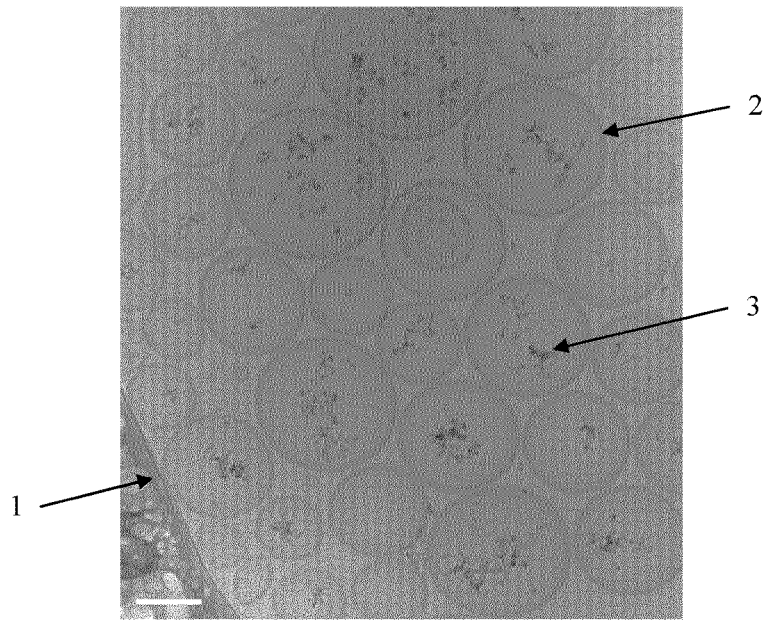
Figure 4:
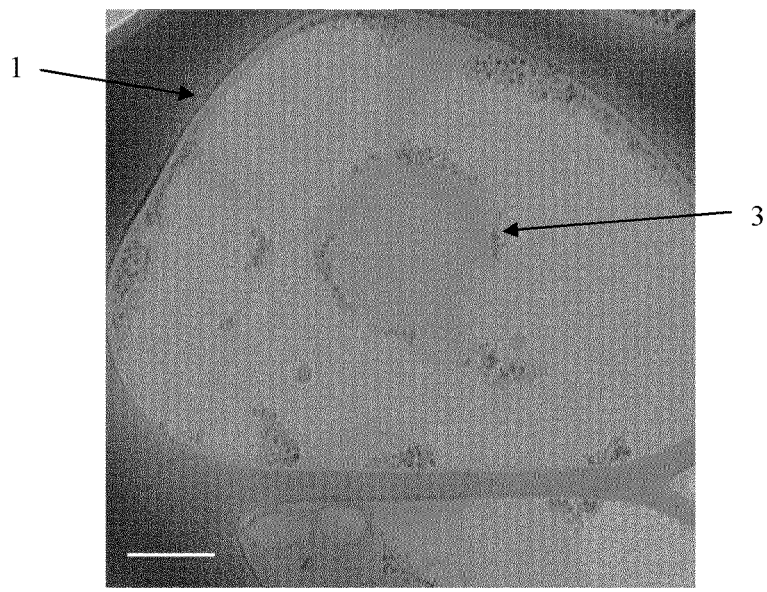
Figure 4:
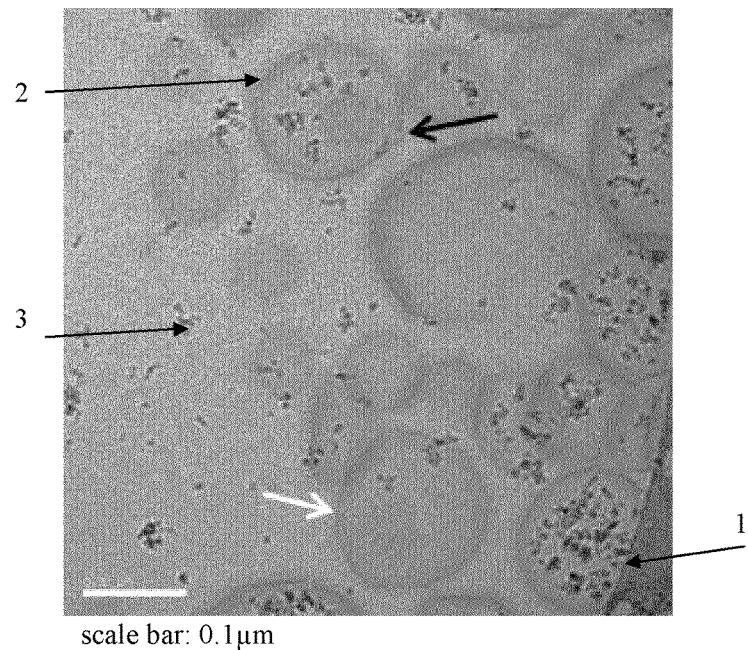
Figure 4:
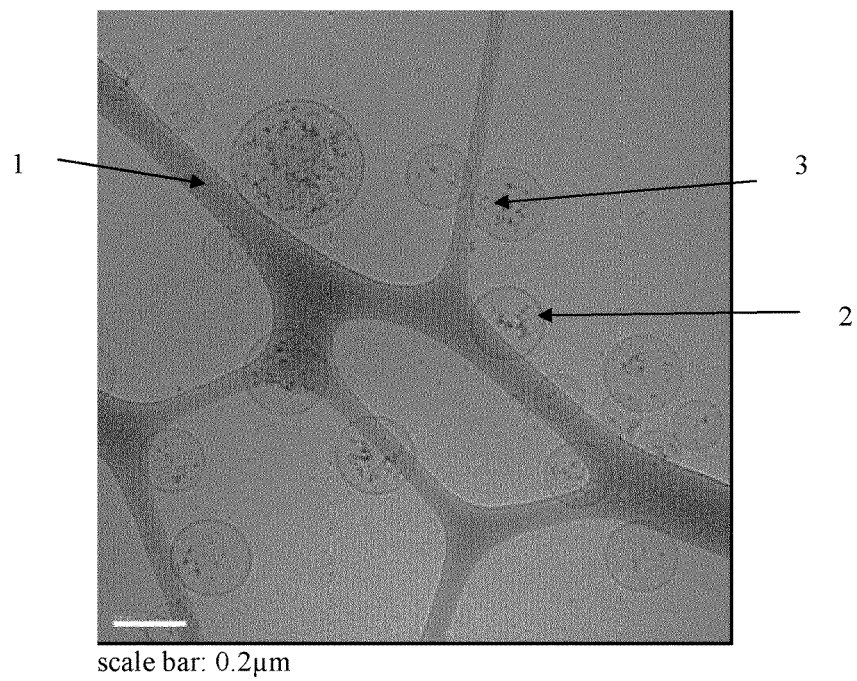
Figure 4:
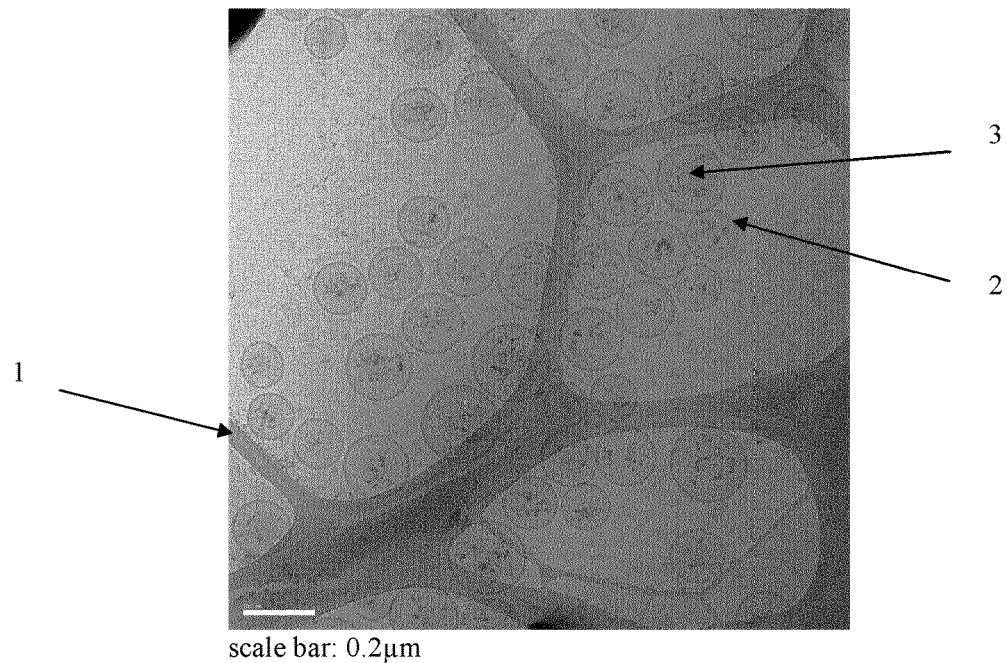

FIG. 4A shows non-thermosensitive liposomes loaded with iron oxide nanoparticles (example 4.2) aged at room temperature FIG. 4B shows non-thermosensitive liposomes loaded with iron oxide nanoparticles (example 4.2) aged at 60° C.

FIG. 4C shows thermosensitive liposomes loaded with iron oxide nanoparticles (example 4.1) aged at room temperature.

FIG. 4D shows iron oxide nanoparticles released from thermosensitive liposomes after aging at 43° C. (Tm) (example 4.1).

FIG. 4E shows iron oxide nanoparticles released from thermosensitive liposomes after aging at 48° C. (above Tm) (example 4.1).

FIG. 4F shows thermosensitive liposomes loaded with iron oxide nanoparticles (example 4.3) aged at room temperature.

FIG. 4G shows thermosensitive liposomes loaded with iron oxide nanoparticles (example 4.3) aged at 43° C. (Tm).

DETAILED DESCRIPTION OF THE INVENTION

The inventors herein provide a thermosensitive liposome disrupting at Tm (gel-to-liquid crystalline phase transition temperature) or above Tm. This liposome comprises a thermosensitive lipidic membrane encapsulating nanoparticles usable, in a subject, as a therapeutic or diagnostic agent.

The inventors surprisingly observed a disruption of the thermosensitive liposome at Tm or above Tm when the electrostatic surface charge of nanoparticles is below −20 mV or above +20 mV when measured in an aqueous medium at physiological pH (typically between pH 6 and pH 8). This disruption of the liposome membrane allows the release of the encapsulated charged nanoparticles.

As used herein, the term "subject" means any organism. The term need not refer exclusively to a human being, which is one example of a subject, but can also refer to animals, in particular warm-blooded vertebrates, typically mammals, and even tissue cultures.

Liposomes

The term "liposome" refers to a spherical vesicle composed of at least one bilayer of amphipathic molecules which forms a membrane separating an intravesicular medium from an external medium. The intravesicular medium constitutes the internal aqueous core of the liposome. Hydrophilic molecules or components can be encapsulated inside the internal aqueous core of the liposome via active methods of encapsulation known by the skilled person and further herein below described. Hydrophobic molecules or components can be entrapped inside the membrane.

Figure 1:
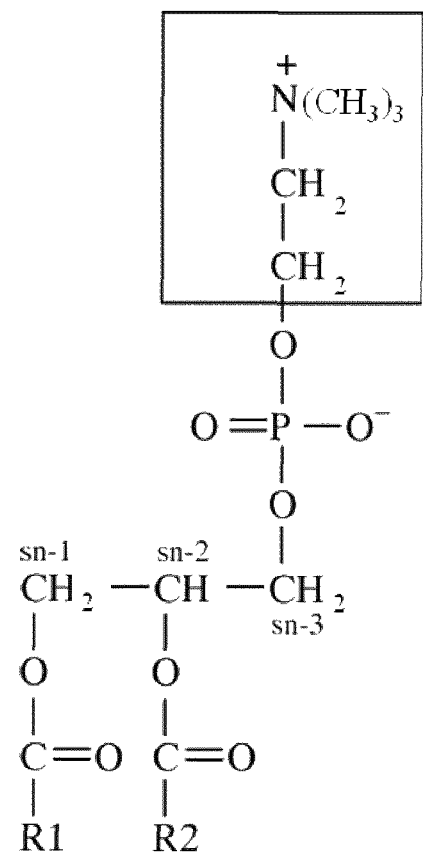
FIG. 1: Schematic structure of a phosphatidylcholine molecule.

The amphipathic molecules constituting the bilayer are lipids, more particularly phospholipids. The amphipathic characteristic of phospholipid molecules lies in the presence of a hydrophilic head, constituted of a phosphate group and a glycerol group, and a hydrophobic tail, constituted of one or two fatty acids (see FIG. 1).

In an aqueous medium, phospholipids tend to self-assemble to minimize contact of the fatty acyl chains with water, and they tend to adopt different types of assembly (micelles, lamellar phase, etc.) according to their chemical structure. More particularly, phosphatidylcholines are known to form a lamellar phase consisting of stacked bilayers undergoing a "spontaneous" curvature and finally forming vesicles (Lasic, D. D. et al., Adv. Colloid. Interf. Sci., 2001, 89-90:337-349). The phospholipidic lamellar phase constitutes a thermotropic liquid crystal. This means that the ordering degree of the amphipathic molecules depends on the temperature. Indeed, a phospholipidic bilayer demonstrates a main phase transition temperature $T_m$ (for temperature of "melting"), corresponding to a transition between the "gel-like" lamellar phase $L_\beta$ to the "fluid-like" lamellar phase $L_\alpha$. In the "gel" phase, strong hydrophobic interactions between the carbonated chains of the fatty acids provoke a crystalline ordering of phospholipid molecules: the bilayer is only permeable to small ions. In the "fluid" phase, the hydrophobic tails are moving due to the thermal motion, which causes a loss of ordering of the phospholipid molecules and leads to a "liquid crystalline" phase: the bilayer becomes permeable to molecules such as a drug.

The "gel-to-liquid crystalline" phase transition temperature $T_m$ depends on the chemical structure of the phospholipid molecule: hydrocarbon chain length, unsaturation, asymmetry and branching of fatty acids, type of chain-glycerol linkage (ester, ether, amide), position of chain attachment to the glycerol backbone (1,2-vs 1,3-) and head group modification.

In the case of phosphatidylcholines, the structure and conformation of fatty acyl chains is of particular relevance (Koynova et al., Biochim. Biophys. Acta, 1998, 1376:91-145).

Increasing the chain length of fatty acids increases the main phase transition temperature. For example, it was shown that for saturated diacyl phosphatidylcholines with chain lengths ranging from 9 to 24 carbon atoms, $T_m$ is linearly dependent on 1/n (n being the number of carbon atoms in the fatty acyl chains), with $T_m$ increasing from, i.e., 41° C. for n=16 to 80° C. for n=24.

The effect of unsaturation on the main gel-to-liquid crystalline phase transition temperature depends on the conformation (cis or trans type), the position in the fatty acyl chains and the number of double bonds. For example, introducing a single site of unsaturation of the cis type on the sn-2 chain only and in both chains of a phosphatidylcholine comprising 18 carbons can have the effect of lowering the chain melting transition temperature by 50° C. (from 54.5° C. to 3.8° C.) and 75° C. (from 54.5° C. to −21° C.), respectively. In contrast, when the double bond is of trans type, the effect is considerably lessened. Further, $T_m$ depends critically on the position of the cis-double bond. Specifically, $T_m$ is minimized when the double bond is located near the geometric center of the hydrocarbon chain, and progressively increases as the double bond migrates toward either end of the chain. These dependencies apply when the double bond is present in the sn-2 chain only or in both chains of phosphatidylcholine. Concerning the influence of the number of double bonds, it was shown that by increasing the number of cis-unsaturation $T_m$ is decreased. For example, when two or three sites of cis-unsaturation are introduced into both acyl chains of a phosphatidylcholine comprising 18 carbons, the chain melting transition temperature is lowered by an impressive 109° C. (from 54.5° C. to −55.1° C.) and 116° C. (from 54.5° C. to −61.5° C.), respectively (Koynova et al., Biochim. Biophys. Acta, 1998, 1376:91-145).

Mixed-chain phosphatidylcholines present different hydrocarbon chain lengths at the sn-1 and sn-2 positions. Empirical equations have been derived that allow for accurate prediction of the transition temperatures of related phosphatidylcholines of defined structure. A normalized chain-length inequivalence parameter, $\Delta C/CL$, has been described, where $\Delta C$ ($=|n_1-n_2+1.5|$) is the effective chain-length difference, and $n_1$ and $n_2$ are the number of carbons in the chains at the sn-1 and sn-2 positions of the glycerol backbone, respectively. CL is the effective length of the longer of the two chains. For phosphatidylcholines demonstrating the same number of total carbon atoms constituting the two chains ($n_1+n_2$=constant), the chain melting temperature decreases monotically when the chain length inequivalence parameter $\Delta C/CL$ is increased to about 0.4. When $\Delta C/CL$ goes above ca. 0.4, packing perturbation, caused by the methyl ends of the acyl chains, becomes so overwhelming that the asymmetric phosphatidylcholine molecules adopt a new packing arrangement referred to as mixed interdigitation. Upon this rearrangement, $T_m$ increases with chain length asymmetry.

For drug delivery purposes, a sterol component may be included to confer the liposome suitable physicochemical and biological behavior. Such a sterol component may be selected from cholesterol or its derivative, e.g., ergosterol or cholesterolhemisuccinate, but it is preferably cholesterol.

Cholesterol is often used in lipidic formulation of liposomes because it is generally recognized that the presence of cholesterol decreases their permeability and protects them from the destabilizing effect of plasma or serum proteins.

The cholesterol molecule contains three well-distinguished regions: a small polar hydroxyl group, a rigid plate-like steroid ring, and an alkyl chain tail. When cholesterol intercalates into the membrane, its polar hydroxyl groups positioned near the middle of the glycerol backbone region of the phosphatidylcholine molecule (Kepczynski, M. et al., Chemistry and Physics of Lipids, 2008, 155:7-15). Incorporation of modifiers such as cholesterol into the lipid bilayers changes greatly the structural or physical properties of the liposomal membrane such as its organization, free volume, thickness, fluidity (viscosity) and polarity (hydrophobicity).

The bilayer's viscosity depends on the position of cholesterol within the bilayer which influences the free volume of the membrane and the temperature. The effect of cholesterol on the bilayer's microviscosity is rather complex. It is well-known that cholesterol increases the apparent microviscosity (reduces fluidity) of membranes in liquid phase (Cournia et al., J. Phys. Chem. B, 2007, 111:1786-1801).

Papahadjopoulos et al. showed that the protective effect of cholesterol for liposomes depends on the physical state, i.e., "gel" or "fluid", of the lipidic membrane when in contact with serum or plasma. In the gel state, the presence of cholesterol affects the ordering parameter of the phospholipid acyl chains within the bilayer and enhances the release of entrapped molecules. In the fluid state, cholesterol stabilizes the liposomes and prevents leakage of encapsulated material (Papahadjopoulos et al., Pharm. Research, 1995, 12(10):1407-1416).

Upon addition of cholesterol in a concentration above 25 molar percentage (mol %), there is a dramatic influence on the gel-to-liquid crystal lipid-phase transition. A new thermodynamically stable region of coexistence between the liquid-disordered (fluid) and solid-ordered (gel) phase is described: the liquid-ordered phase (Cournia et al., J. Phys. Chem. B, 2007, 111:1786-1801; Polozov et al., Biophysical Journal, 2006, 90:2051-2061). This new phase is characterized by a fluidity which is intermediate between the fluidity of the gel phase and the fluidity of the fluid phase formed by the pure lipids. Recently, it has been proposed that the liquid-ordered phase is formed when cholesterol associates with saturated, high-melting lipids, such as dipalmitoylphosphatidylcholine (DPPC) and sphingomyelin, to create dynamic complexes in model membranes, so-called "lipid-rafts". Cholesterol promotes a phase separation in model membranes where cholesterol-rich and cholesterol-poor microdomains are formed (Radhakrishnan et al., Proc. Natl. Acad. Sci., 2000, 97:12422-12427; McConnell et al., Biochim. Biophys. Acta, 2003, 1610:159-173). Indeed, Gaber et al. (Pharm. Research, 1995, 12(10):1407-1416) showed that two lipidic formulations containing 33 mol % of cholesterol dipalmitoylphosphatidylcholine (DPPC), hydrogenated soybean phosphatidylcholine (HSPC) and cholesterol, in the molar ratio of 100:50:75 and 50:50:50 respectively, do not present a phase transition temperature between 30° C. and 65° C., as demonstrated by differential scanning calorimetry measurements. Liposomes with such a formulation are called "non-thermosensitive" liposomes.

Typical "thermosensitive" liposomes usable in the context of the present invention (i.e., liposomes with a main phase transition temperature $T_m$ typically comprised between 39° C. and 55° C., preferably between 39° C. and 50° C., even more preferably between 39° C. and 45° C.) comprise at least a phosphatidylcholine.

The phosphatidylcholine may be selected from dipalmitoylphosphatidylcholine (DPPC), distearylphosphatidylcholine (DSPC), hydrogenated soybean phosphatidylcholine (HSPC), monopalmitoylphosphatidylcholine (MPPC), monostearylphosphatidylcholine (MSPC) and any mixture thereof.

In a preferred embodiment the thermosensitive liposome further comprises distearylphosphatidylethanolamine (DSPE), distearylphosphatidylethanolamine (DSPE)-methoxypolyethylene glycol (PEG) (DSPE-PEG).

In a preferred embodiment, cholesterol is added in a molar ratio inferior to 25 mol %.

A preferred thermosensitive lipidic membrane comprises dipalmitoylphosphatidylcholine (DPPC), hydrogenated soybean phosphatidylcholine (HSPC), cholesterol and distearylphosphatidylethanolamine (DSPE)-methoxypolyethylene glycol (PEG), for example PEG2000 (DSPE-PEG2000).

In a particular embodiment, the molar ratio of the previously identified compounds is preferably 100:50:30:6 or 100:33:27:7.

Another preferred thermosensitive lipidic membrane comprises dipalmitoylphosphatidylcholine (DPPC), monopalmitoylphosphatidylcholine (MPPC) and distearylphosphatidylethanolamine (DSPE)-methoxypolyethylene glycol (PEG), for example methoxypolyethylene glycol 2000 (DSPE-PEG2000).

In a particular embodiment, the molar ratio of the previously identified compounds is preferably 100:12:5.

Another preferred thermosensitive lipidic membrane comprises dipalmitoylphosphatidylcholine (DPPC), monostearylphosphatidylcholine (MSPC), and distearylphosphatidylethanolamine (DSPE)-methoxypolyethylene glycol (PEG), for example methoxypolyethylene glycol 2000 (DSPE-PEG2000).

In a particular embodiment, the molar ratio of the previously identified compounds is preferably 100:12:5.

Depending on the mode of preparation, the size and the degree of lamellarity of the vesicles can be tuned. Several methods for preparing unilamellar lipidic vesicles have been described in the literature, such as reverse phase evaporation (Szoka et al., PNAS, 1978, 75(9):4191-4198), ethanol injection (Pons et al., International Journal of Pharmaceutics, 1993, 95(1-3):51-56), heating (Mozafari et al., Journal of Biotechnology, 2007, 129:604-613), but the most simple is the lipid film hydration method (Bangham et al., J. Mol. Biol., 1965, 13:238-252).

Briefly, in the lipid film hydration method, lipids are solubilized in an organic solvent such as chloroform. After homogenization of the solution, the organic solvent is evaporated under a nitrogen stream. The as-obtained dried lipid film is then hydrated by an aqueous medium at a temperature above the main phase transition temperature $T_m$ leading to the formation of multilamellar vesicles with sizes ranging from 100 to 800 nm (Mills, J. K. et al., Methods in Enzymology, 2004, 387:82-113). Cycles of dehydration and rehydration, by respectively freezing (in liquid nitrogen) and thawing the solution (at a temperature above $T_m$), allow increasing the aqueous internal volume by forming unilamellar vesicles. A process allowing vesicle size calibration is then applied to obtain a homogeneous size distribution. Sonication produces Small Unilamellar Vesicles (SUV) with sizes ranging from 20 to 50 nm, whereas an extrusion process through a filter membrane produces Large Unilamellar Vesicles (LUV) with sizes ranging from 50 to 500 nm depending on the size of the filter pores. Both processes, sonication and extrusion, have to be performed at a temperature above $T_m$.

The largest size of the thermosensitive liposomes according to the present invention is typically comprised between 50 and 500 nm, preferably between 50 and 250 nm, for example between about 50 nm and about 150 nm.

Thermosensitive liposomes used in the present invention preferably comprise a biocompatible coating to ensure or improve their biocompatibility and specific biodistribution.

The biocompatible coating allows or favors the liposomes' stability in a biocompatible suspension, such as a physiological fluid (blood, plasma, serum, etc.) or any isotonic media or physiological medium, for example media comprising glucose (5%) and/or NaCl (0.9%), which is required for a pharmaceutical administration.

Such a biocompatible coating is obtained by treating the liposome with a surface treating agent.

Stability may be confirmed by dynamic light scattering measurements of the liposomes in biocompatible suspension.

Said coating advantageously preserves the integrity of the liposome in vivo, ensures or improves its biocompatibility, and facilitates its optional functionalization (for example with spacer molecules, biocompatible polymers, targeting agents, proteins, etc.).

The coating can be non-biodegradable or biodegradable. Both options can be used in the context of the present invention.

Examples of non-biodegradable coatings are one or more materials or surface treating agents selected from the group consisting of sugar (for example, agarose), saturated carbon polymers (for example, polyethylene oxide), reticulated or not, modified or not (for example, polymethacrylate or polystyrene), as well as combinations thereof.

Examples of biodegradable coatings are for example one or more materials or surface treating agents selected from the group consisting of a biological molecule, modified or not, natural or not and, a biological polymer, modified or not, of natural shape or not. The biological polymer may be a saccharide, an oligosaccharide or a polysaccharide, polysulfated or not, for example dextran.

The aforementioned materials, compounds or surface treating agents can be used alone or in combinations, mixtures or assemblies, composite or not, covalent or not, optionally in combination with other compounds.

Thermosensitive liposomes according to the present invention can further comprise a surface component enabling specific targeting of biological tissues or cells. Such a surface component is preferably a targeting agent allowing the liposome to interact with a recognition element present on the target biological structure.

Such targeting agents can act only once the liposomes are accumulated in the tumor. As the conformation of the targeting agent will be responsible for its interaction with the target, the density of said targeting agent is to be controlled carefully according to methods known by the skilled person. A high density thereof can indeed perturb the targeting agent conformation and in consequence its recognition by the target cell (see for example J. A. Reddy et al., Gene Therapy, 2002, 9:1542; Ketan B. Ghaghada et al., Journal of Controlled Release, 2005, 104:113). In addition, a high target agent density may favor liposomes' clearance by the reticuloendothelial system (RES) during circulation in the vasculature.

The coating can also contain different functional groups (or linker segments), allowing any molecule of interest to bind to the surface of the liposome, such as a surface component enabling specific targeting of biological tissues or cells.

Nanoparticles

The products and compositions of the invention can be used in many fields, in particular human and veterinary medicine.

The encapsulated nanoparticle may be used, once released from the thermosensitive liposome, as a therapeutic or diagnostic agent and its structure will directly depend from its intended function.

The term "nanoparticle" refers to a particle or aggregate of particles, said nanoparticle comprising a core (or central core) and a coating, the largest dimension of the core being less than about 100 nm. Typically, the largest dimension of the core of the nanoparticle is the diameter of a nanoparticle of round or spherical shape, or the longest length of a nanoparticle of ovoid or oval shape.

The terms "size of the nanoparticle" and "largest size of the nanoparticle" herein refer to the "largest dimension of the core of the nanoparticle".

The "core" can designate a single particle (crystal or crystallite) or an aggregate of particles (aggregate of crystal or crystallites).

Figure 2:
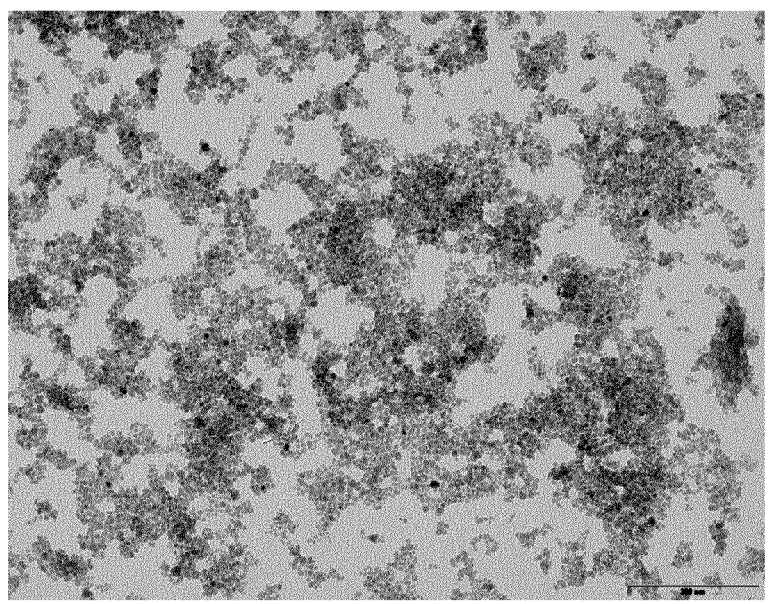
FIGS. 2A and 2B: Transmission electron microscopy (TEM) images of iron oxide nanoparticles.
Figure 2:
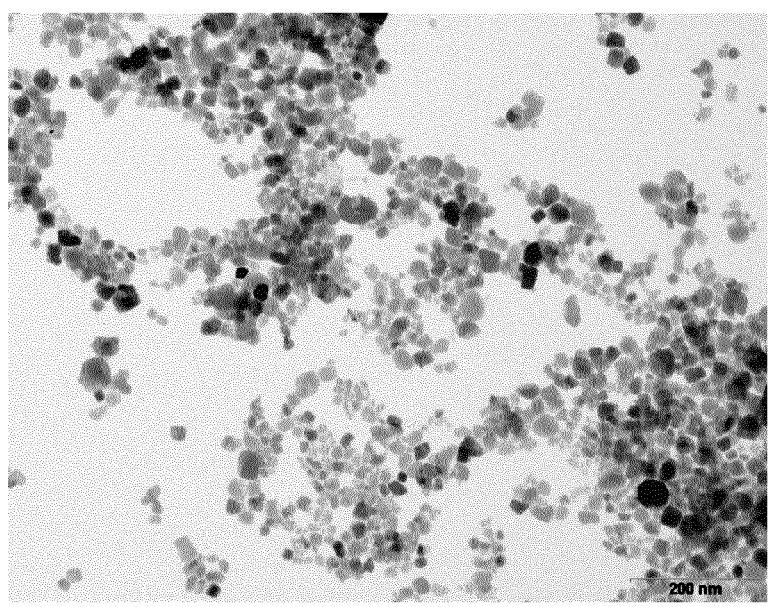

Transmission Electron Microscopy (TEM) or cryoTEM can be advantageously used to measure the size of the core of the nanoparticle, especially when the core consists of a single particle (see FIG. 2). Also, Dynamic Light Scattering (DLS) can be used to measure the hydrodynamic diameter of the core of the nanoparticle in solution when said core consists of a particle or an aggregate of particles. These two methods may further be used one after each other to compare size measurements and confirm said size.

The central core of the nanoparticle is typically prepared from a therapeutic or diagnostic material, which is preferably an activable or excitable material. The material can be an inorganic material, an organic material or a mixture thereof. The material is preferably an inorganic material.

Any kind of nanoparticle may be encapsulated in the thermosensitive liposome of the present invention so long as its electronic surface charge is below −15 mV or above +15 mV, for example between −15 mV and −20 mV or between +15 mV and +20 mV, typically below −20 mV or above +20 mV, when determined by zeta potential measurements, performed on nanoparticle suspensions with concentrations varying between 0.2 and 8 g/L, the nanoparticles being suspended in an aqueous medium at a pH comprised between 6 and 8.

The nanoparticle's shape can be for example round, flat, elongated, spherical, ovoid or oval, and the like. The shape can be determined or controlled by the method of production, and adapted by the person of the art according to the desired applications.

As the shape of the particles can influence their "biocompatibility" once delivered on the targeted site, particles having a quite homogeneous shape are preferred. For pharmacokinetic reasons, nanoparticles being essentially spherical, round or ovoid in shape are thus preferred. Spherical or round shape is particularly preferred.

The largest size of the nanoparticles, i.e., the largest dimension of the core of the nanoparticles, used in the context of the present invention is typically comprised between 1 and 100 nm.

When nanoparticles are used as a therapeutic agent, it is advantageously comprised between about 5 nm and about 100 nm, for example between about 5 nm and 80 nm, for example between about 10 nm and about 80 nm, advantageously between about 10 or 20 nm and about 70 nm, preferably between about 15 nm and about 60 nm or between about 10 or 15 nm and about 50 nm.

When nanoparticles are used as a diagnostic agent, it is advantageously comprised between about 2 nm and about 10 nm, for example between about 4 nm and about 8 nm.

The nanoparticles used in the context of the present invention comprise a core and a coating, said coating being responsible for the presence of an electrostatic surface charge below −20 mV or above +20 mV when measured in an aqueous medium at physiological pH.

The electrostatic coating is advantageously a "full coating" (complete monolayer). This implies the presence of a very high density of biocompatible molecules creating an appropriate charge on the entire surface of the nanoparticle. Such a full coating will favor the disruption of the membrane of the thermosensitive liposome at Tm or above Tm.

The inorganic material constituting the core may be a magnetic material.

Magnetic materials include for example iron, nickel, cobalt, gadolinium, samarium, and neodymium, preferably in the form of an oxide, a hydroxide or a metal, and any mixture thereof.

In specific examples, the material forming the core is selected from the group consisting of ferrous oxide and ferric oxide. In a preferred embodiment of the present invention, the oxide nanoparticles are made of magnetite or maghemite.

Mixed material can also be used to optimize interactions between a magnetic field and nanoparticles. Solid solution forms (well-known by one skilled in the art as random mixtures of several materials), such as $CoFe_2O_4$, can be used as a mixed material. Solid solution forms in demixed phases, such as $Fe_2O_3/Co$, can further be used.

When the magnetic material is used as a therapeutic material, it is preferably a ferromagnetic material.

When the magnetic material is used as a diagnostic material, it is preferably a superparamagnetic material.

The inorganic material constituting the core may be a high electronic density material constituted by a metallic element having an atomic number (Z) of at least 50, preferably at least 60 or 61, more preferably at least 65, 66, 67 or even 68.

The atomic number (also known as the proton number) is the number of protons found in the nucleus of an atom. It is traditionally represented by the symbol Z. The atomic number uniquely identifies a chemical element. In an atom of neutral charge, atomic number is equal to the number of electrons.

Z participates in the incoming radiation absorption capacity of nanoparticles.

The inorganic material constituting the core may be an oxide selected from Cerium (IV) oxide ($CeO_2$), Neodynium (III) oxide ($Nd_2O_3$), Samarium (III) oxide ($Sm_2O_3$), Europium (III) oxide ($Eu_2O_3$), Gadolinium (III) oxide ($Gd_2O_3$), Terbium (III) oxide ($Tb_2O_3$), Dysprosium (III) oxide ($Dy_2O_3$), Holmium oxide ($Ho_2O_3$), Erbium oxide ($Er_2O_3$), Thulium(III) oxide ($Tm_2O_3$), Ytterbium oxide ($Yb_2O_3$), Lutetium oxide ($lu_2O_3$), Hafnium (IV) oxide ($HfO_2$), Tantalum (V) oxide ($Ta_2O_5$), and Rhenium (IV) oxide ($ReO_2$).

In the context of the present invention, mixture of inorganic oxide is also possible.

The inorganic material constituting the core may be a metal, the metal preferably having an atomic number (Z) of at least 40 or 50, more preferably at least 60 or 70.

The metal may be selected from gold (Au—Z=79), silver (Ag—Z=47), platinum (Pt—Z=78), palladium (Pd—Z=46), tin (Sn—Z=50), tantalum (Ta—Z=73), ytterbium (Yb—Z=70), zirconium (Zr—Z=40), hafnium (Hf—Z=72), terbium (Tb—Z=65), thulium (Tm—Z=69), cerium (Ce—Z=58), dysprosium (Dy—Z=66), erbium (Er—Z=68), europium (Eu—Z=63), holmium (Ho—Z=67), lanthanum (La—Z=57), neonydium (Nd—Z=60), praseodymium (Pr—Z=59), and any mixture thereof.

In a preferred embodiment of the present invention, the core of the nanoparticle consists of gold.

In the context of the present invention, the core of the nanoparticle may consist of a mixture of an inorganic oxide and a metal.

The coating responsible for the presence of an electrostatic surface charge below −20 mV or above +20 mV of the nanoparticle when measured in an aqueous medium at physiological pH can be an inorganic or organic surface coating.

When inorganic, the coating may be selected from the group consisting of an oxide, a hydroxide, and an oxyhydroxide. The inorganic coating may comprise for example silicium, aluminum, calcium and/or magnesium.

An inorganic agent selected from the group consisting of, for example, magnesium and calcium will bring a positive charge (above +20 mV) to the surface of the nanoparticle at pH 7.

In another embodiment, a silicium group may be used to bring a negative charge (below −20 mV) to the surface of the nanoparticle at pH 7.

When organic, the coating is prepared with a molecule capable of interacting, through covalent binding or electrostatic binding, with the nanoparticle surface and giving surface properties to said nanoparticle.

The surface-coating organic molecule has two groups, R and X. The function of X is to interact with the nanoparticle surface and the function of R is to give the nanoparticle's surface its specific properties.

X may be selected for example from a carboxylate (R—COO−), a silane (R—Si(OR)$_3$), a phosphonic (R—PO(OH)$_2$), a phosphoric (R—O—PO(OH)$_2$), a phosphate (R—PO$_4^{3-}$) and a thiol (R—SH) group.

R brings at least the electronic surface charge to the nanoparticle in aqueous suspension at a physiological pH.

When R brings a positive charge to the nanoparticle's surface, R may be an amine ($NH_2$—X).

When R brings a negative charge to the nanoparticle's surface, R may be a phosphate ($PO_4^{3-}$—X) or a carboxylate (COO−—X).

An organic coating conferring a positive charge (above +20 mV) to the nanoparticles' surface may be selected from, for example, aminopropyltriethoxisilane, polylysine or 2-aminoethanethiol.

An organic coating conferring a negative charge (below −20 mV) to the nanoparticles' surface may be selected from, for example, a polyphosphate, a metaphosphate, a pyrophosphate, etc., or from citrate or dicarboxylic acid, in particular succinic acid.

Again, the electrostatic coating is advantageously a "full coating".

This electrostatic coating and especially amino or carboxylic moieties can further be used to link any group on the nanoparticle's surface. For example, it may be used to link a targeting group or a coupling group as herein described on the nanoparticle's surface using for example a linker such as a carbodiimide.

Optionally, the nanoparticle surface can be functionalized using a group ("coupling group") able to interact directly with proteins when nanoparticles are released from the thermosensitive liposomes and form a covalent bond with them.

R may be made of a reactive group capable of covalently interacting with amine, carboxyl or thiol groups present on proteins, such as a succinimidyl ester group (which reacts with amine groups) and/or a maleimide group (which reacts with carboxylic groups).

Optionally, the nanoparticle surface can be functionalized using a group ("targeting group") able to target a specific biological tissue or cell. The targeting group can be any biological or chemical structure displaying affinity for a molecule present in the human or animal body.

Such a targeting group typically acts once the nanoparticles are accumulated on the target site and released from the liposome upon thermal activation at Tm or above Tm.

The targeting group may be selected from an antigen, a spacer molecule, and a biocompatible polymer. The targeting group can be any biological or chemical structure displaying affinity for molecules present in the human or animal body. For instance it can be a peptide, oligopeptide or polypeptide, a protein, a nucleic acid (DNA, RNA, SiRNA, tRNA, miRNA, etc.), a hormone, a vitamin, an enzyme or the like and in general any ligand of molecules (for example receptors, markers, antigens, etc.). Ligands of molecules are expressed by pathological cells, in particular ligands of tumor antigens, hormone receptors, cytokine receptors or growth factor receptors. Said targeted groups can be selected for example from the group consisting of LHRH, EGF, a folate, anti-B-FN antibody, E-selectin/P-selectin, anti-IL-2Rα antibody, GHRH, etc.

Electrostatic coating and/or coupling groups as herein described can be used to link any group on the nanoparticle's surface. For example, they may be used as linkers to graft a targeting group on the nanoparticle's surface.

A particular object herein described is thus a thermosensitive liposome encapsulating nanoparticles which are covalently or electrostatically coated with an agent responsible for the presence of the electrostatic surface charge below −20 mV or above +20 mV.

This agent is preferably an organic molecule having two groups, R and X, R being selected from an amine, a phosphate and a carboxylate and X being selected from a carboxylate, a silane, a phosphonic, a phosphoric, and a thiol.

The nanoparticle can further comprise a coupling group selected from a succinimidyl ester and a maleimide group and/or a targeting group selected from a peptide, an oligopeptide, a polypeptide, a protein, a nucleic acid, a hormone, a vitamin, an enzyme, a ligand of a tumor antigen, a hormone receptor, a cytokine receptor and a growth factor receptor.

Optionally, the nanoparticle surface can be functionalized using a steric group. Such a group may be selected from polyethylene glycol (PEG), polyethylenoxide, Polyvinylalcohol, Polyacrylate, Polyacrylamide (poly(N-isopropylacrylamide)), Polycarbamide, a biopolymer or polysaccharide such as Dextran, Xylan, cellulose, or collagen, and a zwitterionic compound such as polysulfobetaine, etc.

This steric group increases the nanoparticles' stability in a biocompatible suspension, such as a physiological fluid (blood, plasma, serum, etc.) or any isotonic media or physiological media, for example media comprising glucose (5%) and/or NaCl (0.9%).

From the teachings of the present invention, those skilled in the art will recognize that the nanoparticles may be modified without departing from the spirit of the invention.

Typical methods for the production of nanoparticles or nanoparticle aggregates usable in the context of the present invention are described for example in WO2007/118884, WO 2009/147214, U.S. Pat. No. 6,514,481 B1, WO2011/003999, and Liu et al., Journal of Magnetism and Magnetic Materials, 2004, 270:1-6, *"Preparation and characterization of amino-silane modified superparamagnetic silica nanospheres"*.

Therapeutic Uses

The therapeutic nanoparticles' efficiency is increased if nanoparticles are internalized by target cells or are in contact with them. To reach this aim, the nanoparticles' surface properties are typically modified to favor an interaction with the target cell. For example, the electric charge of the nanoparticle surface may be modified or the surface may be linked to a targeting group or agent such as herein described.

Specific binding interactions are those of surface ligands (targeting groups as herein described) which allow the nanoparticle to specifically interact with complementary molecules or receptors on the cell membrane. These interactions induce a receptor-mediated endocytosis. A targeting ligand conjugated to the surface of nanoparticles can recognize and bind receptors, membrane proteins, and surface antigens expressed on the target cell, thereby triggering endocytosis and intracellular delivery.

Non-specific attractive forces that promote cellular contact and particle uptake result from intrinsic nanoparticle characteristics such as surface charge.

However, most of time, such modifications are detrimental to the nanoparticles' biodistribution.

The herein-described thermosensitive liposomes overcome this problem and allow, as explained previously, the efficient biodistribution (delivery) and controlled release of therapeutic nanoparticles in the subject's body. These liposomes favor the concentration of nanoparticles, in particular of nanoparticles exhibiting modified surface properties, on the target site.

A controlled (spatial and time) release of nanoparticles is now possible, i.e., the nanoparticle is delivered where and at the moment it is needed when its therapeutic activity depends on its interaction with cells (nanoparticle in contact with cells and/or internalized within cells).

When the nanoparticle is used as a therapeutic tool, its core is prepared with a therapeutic material which may be an externally activable material, i.e., a material which may be activated by an external energy source. In a particular embodiment, the therapeutic material is capable of functionally disturbing, altering or destructing a target cell, tissue or organ.

The therapeutic material may be selected from a high-electronic-density material and a magnetic material as described previously.

The activation source can be an ionizing radiation source for a nanoparticle the core of which is prepared with a high-electronic-density material such as $HfO_2$ or Au.

Ionizing radiation is typically of about 5 KeV to about 25,000 KeV, in particular of about 5 KeV to about 6000 KeV (LINAC source), or of about 5 KeV to about 1500 KeV (such as a cobalt 60 source). Using an X-ray source, particularly preferred ionizing radiation is typically of about 50 KeV to about 12,000 KeV, for example of about 50 KeV to about 6000 KeV.

The required doses of ionizing radiation are preferably doses comprised between about 0.05 Gray and about 16 Grays, preferably between about 0.05 Gray and about 6 Grays, for applications performed in vitro.

Doses are comprised between more than about 0.05 Gray and less than about 16 or 30 Grays for applications performed, in particular, locally, ex vivo or in vivo.

Total ionizing radiation ranges from about 1.5 Gray up to about 85 Grays in a human according to the current practice. An additional irradiation boost of about 40 Grays may also be provided in a human, according to the current practice.

The total dose of radiation delivered can be given following different schedules such as single dose, fractionated doses, hyperfractionated doses, etc.

In general and in a non-restrictive manner, the following X-rays can be applied in different cases to activate the nanoparticles:

X-rays of 50 to 150 keV which are particularly efficient for a superficial target tissue;

X-rays (orthovoltage) of 200 to 500 keV which can penetrate a tissue thickness of 6 cm; and X-rays (megavoltage) of 1000 keV to 25,000 keV. For example the ionization of nanoparticles for the treatment of prostate cancer can be carried out via five focused X-rays with an energy of 15,000 keV.

Radioactive isotopes can alternatively be used as a ionizing radiation source (named as curietherapy or brachytherapy). In particular, Iodine $I^{125}$ (t ½=60.1 days), Palladium $Pd^{103}$ (t ½=17 days), Cesium $Cs^{137}$ and Iridium $Ir^{192}$ can advantageously be used.

Immunoradionuclides (or immunoradiolabeled ligands) can also be used as an ionizing radiation source in the context of radioimmunotherapy. Suitable radionuclides for radioimmunotherapy may be, for example, selected from $^{131}I$, $^{186}Re$, $^{177}Lu$ or $^{90}Y$.

Charged particles such as proton beams and ion beams such as carbon, in particular high-energy ion beams, can also be used as an ionizing radiation source.

Electron beams may also be used as an ionizing radiation source with energy comprised between 4 MeV and 25 Mev.

Specific monochromatic irradiation sources could be used in order to selectively generate X-rays with an energy close to or corresponding to the desired X-ray absorption edge of the atom(s) of the nanoparticle.

Preferentially sources of ionizing radiation may be selected from Linear Accelerator (LINAC), Cobalt 60 and brachytherapy sources.

Amounts (range of total dose of irradiation) and schedules (planning and delivery of irradiation in a single dose, or in the context of a fractioned or hyperfractionated protocol, etc.) are defined for any disease/anatomical site/disease stage/patient setting/patient age (child, adult, elderly patient), and constitute the standard of care for any specific situation.

The irradiation can be applied at any time after release of the nanoparticles, on one or more occasions, by using any currently available system of radiotherapy.

In a particular embodiment, the therapeutic material is a magnetic oxide (magnetite or maghemite), in particular a ferromagnetic material, and the activation source is a magnetic field source.

The magnetic field, which is preferably non-oscillating or stable, can be applied constantly after the release of nanoparticles, at one or more times, by using any magnetic field source.

The magnetic field source is preferably a uniform and unidirectional magnetic field source and may be selected from any permanent magnet, electromagnet and Magnetic Resonance Imaging (MRI) equipment.

A suitable non-oscillating or stable magnetic field is available in standard MRI equipment which typically has a magnetic field in the range of 0.5 to 5 Teslas.

When exposed to a magnetic field, and depending on the duration of the exposure, magnetic nanoparticles allow cell or tissue destruction (duration of several minutes, for example from 2 or 5 minutes to 120 minutes).

The nanoparticles or nanoparticle aggregates and compositions of the present invention can be advantageously used for lysis of cancer cells or cells suspected to be the same, when subjected to a magnetic field.

The inventors herein disclose the use of a nanoparticle as herein described, or a population of identical or different nanoparticles as herein described, to prepare a pharmaceutical composition intended to treat a subject in need thereof.

The term "treatment" denotes any action performed to correct abnormal functions, to prevent diseases, or to improve pathological signs, such as in particular a reduction in the size or growth of an abnormal tissue, in particular of a tumor, a control of said size or growth, a suppression or destruction of abnormal cells or tissues, a slowing of disease progression, a disease stabilization with delay of cancer progression, a reduction in the formation of metastases, a regression of a disease or a complete remission (in the context of cancer, for example), etc.

The pharmaceutical composition may be a composition intended to perturb, disturb, alter or destroy target cells in a subject in need thereof, when said cells are exposed to an activation source.

An object of the invention is a thermosensitive liposome, such as defined hereinabove and/or which can be obtained by the methods herein described, for perturbing, disturbing, altering or destroying target cells when said cells are exposed to an activation source.

A particular thermosensitive liposome according to the present invention is a liposome for preventing or treating a cancer or for alleviating the symptoms of a cancer in a subject.

A particular method herein described is a method for inducing or causing the perturbation, lysis, apoptosis or destruction of cells in a subject, comprising a) administering thermosensitive liposomes (as described hereinabove) containing nanoparticles to the subject, b) heating the thermosensitive liposomes at Tm or above Tm in order to allow the local release of nanoparticles and their subsequent interaction with cells, in particular target cells, and, optionally, c) exposing the cells to an activation source, typically an external activation source such as herein described, said exposure activating the nanoparticles which in turn induce or cause the perturbation, lysis, apoptosis or destruction of the cells.

The thermosensitive liposomes according to the present invention can be administered by different routes such as local (intra-tumoral (IT) for example), subcutaneous, intravenous (IV), intradermic, intra-arterial, airways (inhalation), intraperitoneal, intramuscular and oral routes (per os). The thermosensitive liposomes according to the present invention can further be administered in the virtual cavity of a tumor bed after tumorectomy. A preferred administration route is the intravenous route.

After a given time following injection by the intravenous route of the thermosensitive liposomes, the Enhanced Permeation and Retention ("EPR") effect is responsible for the passive accumulation of the thermosensitive liposomes into the tumor mass. It has indeed been observed that the tumor vessels are quite distinct from normal capillaries and that their vascular "leakiness" encourages selective extravasation of liposomes not usual in normal tissues. The lack of effective tumor lymphatic drainage prevents clearance of the penetrant liposomes and promotes their accumulation.

The present nanoparticles are thus able to successfully target primary as well as metastatic tumors once released from the intravenously administered thermosensitive liposomes.

The target cells can be any pathological cells, that is to say, cells involved in a pathological mechanism, for example proliferative cells, such as tumor cells, stenosing cells (fibroblast/smooth muscle cells), or immune system cells (pathological cell clones). A preferred application is based on the treatment (for example the destruction or functional alteration) of malignant cells or tissue.

Another object of the invention relates to a method for preventing or treating a disorder, in particular a cancer, or alleviating the symptoms of the disorder in a subject or patient, comprising a) administering thermosensitive liposomes to the patient suffering from the disorder or a composition such as herein described comprising such thermosensitive liposomes, b) heating the thermosensitive liposomes at Tm or above Tm in order to allow the local release of nanoparticles and their subsequent interaction with cells, in particular target cells, and c) subsequently treating the subject by exposing said subject to a source of activation as herein described, such exposition leading to an alteration, disturbance or functional destruction of the patient's abnormal cells, thereby preventing or treating the disorder.

Classical cancer management systematically implies the concurrence of multimodality treatments (combination of radiotherapy and chemotherapy for example).

The herein-described nanoparticles exposed to an activation source, for example in the context of radiotherapy, can be used in association with a different cancer therapy protocol. Such a protocol can be selected from the group consisting of surgery, radiosurgery, chemotherapy, and a treatment comprising administration of cytostatic(s), cytotoxic(s), a targeted therapy, a vaccine, and any other biological or inorganic product intended to treat cancer.

The thermosensitive liposomes according to the present invention may encapsulate, together with the nanoparticles herein described, any therapeutic molecule of interest, in particular any known biological or inorganic product intended to treat cancer.

The herein-described nanoparticles can further be used in the context of radiotherapy alone. The increased observed therapeutic efficacy is partly due to the increased concentration of efficient nanoparticles on the target site allowed by their transport via the thermosensitive liposomes of the invention and by their subsequent controlled release.

The invention can be used to treat any type of malignant tumor such as hematological tumors or malignancies and solid tumors, in particular of epithelial, neuroectodermal or mesenchymal origin. In addition, the herein-described liposomes can be used to treat a premalignant lesion or a specific benign disease where radiation therapy is classically used and/or indicated.

The tumor or cancer may be a cancer where radiotherapy is a classical treatment. Such a cancer may be selected in particular from the group consisting of skin cancers, including malignant neoplasms associated with AIDS and melanoma; central nervous system tumors including brain, brain stem, cerebellum, pituitary, spinal canal, eye and orbit; head and neck tumors; lung cancers; breast cancers; gastrointestinal tumors such as liver and hepatobiliary tract cancers, colon, rectal and anal cancers, and stomach, pancreatic, and esophageal cancers; male genitourinary tumors such as prostate, testicular, penile and urethral cancers; gynecological tumors such as uterine cervical, endometrial, ovarian, fallopian tube, vaginal and vulvar cancers; adrenal and retroperitoneal tumors; sarcomas of bone and soft tissue, regardless of the localization; lymphoma; myeloma; leukemia; and pediatric tumors such as Wilms' tumor, neuroblastoma, central nervous system tumors, Ewing's sarcoma, etc.

The invention is applicable, in the context of therapy, to primary tumors or secondary invasions, loco-regional or distant metastases, and in the context of prophylaxis, in order to avoid secondary malignant central nervous system involvement such as the observed invasions (metastases) from melanoma, lung cancer, kidney cancer, breast cancer, etc.

The thermosensitive liposomes can be used at any time throughout the anticancer treatment period. They can be administered for example as a neoadjuvant (before surgical intervention for cancer exeresis) or as an adjuvant (after surgery).

The thermosensitive liposomes can also be used for advanced tumors which cannot be surgically removed.

Repeated injections or administrations of thermosensitive liposomes can be performed, when appropriate.

Diagnostic Uses

The controlled delivery of nanoparticles is also desired for in vivo imaging and/or diagnostic purposes and is now possible when said nanoparticles are encapsulated in the thermosensitive liposomes according to the present invention.

The inventors herein disclose the use of a thermosensitive liposome according to the present invention, in particular a thermosensitive liposome comprising a nanoparticle as herein described, or a population of identical or different nanoparticles as herein described, to prepare a diagnostic composition intended to detect the presence of abnormal tissue or cells, in particular of tumor cells in a subject, preferably when said subject is exposed to an external source of energy.

An object of the invention is a thermosensitive liposome, such as defined hereinabove and/or which can be obtained by the methods herein described, for detecting or visualizing an abnormal cell of a subject when said subject is exposed to an external source of energy.

The diagnostic material may be selected from a high-electronic-density material and a magnetic material as described previously.

When the nanoparticle is used as a diagnostic agent intended to detect or visualize an abnormal tissue or cell, its core advantageously consists of an imaging material.

Such an imaging material may advantageously be selected from any magnetic material, such as ferrous oxide and ferric oxide, as previously defined. For example, the nanoparticles used in the present invention have a core made of $\gamma$-$Fe_2O_3$ (maghemite) or $Fe_3O_4$ (magnetite) visible in MRI.

The imaging material may be also selected from any high-electronic-density material visible under computed tomography scanner (CT scanner), such as $HfO_2$ or Au.

For imaging purposes, the adjunction to nanoparticles of a targeting group as previously described is preferred.

Another object of the invention relates to a method for detecting or visualizing target cells (allowing in particular the diagnosis of a disorder, in particular of a cancer) in a subject or patient suspected to suffer from a disorder, comprising a) administering thermosensitive liposomes to the patient suffering from the disorder or a composition such as herein described comprising such thermosensitive liposomes, b) heating the area of interest at Tm or above Tm-in order to allow the local release of nanoparticles and their subsequent interaction with cells, in particular target cells, and c) subsequently exposing the subject to a source of activation as herein described, such exposure allowing the detection or visualization of the patient's target cells.

In a particular embodiment, the thermosensitive liposomes herein described are able to vehicle targeted nanoparticles (in particular nanoparticles capable of specifically recognizing tumor cells) in blood circulation while avoiding recognition by the reticuloendothelial system (RES).

If a tumor mass is present, nanoparticles, released from the thermosensitive liposomes at Tm or above Tm, will enter the tumor and interact with the targeted cancer cells. Nanoparticle accumulation provokes a signal perturbation visible in MRI for magnetic nanoparticles or a CT scanner signal increase if high-density nanoparticles are used.

If there is no tumor mass, nanoparticles will be eliminated from blood circulation via the kidneys and no signal increase or perturbation will be detected or visualized.

The inventors further herein disclose the use of a thermosensitive liposome according to the present invention, in particular a thermosensitive liposome comprising a nanoparticle as herein described, or a population of identical or different nanoparticles as herein described, to prepare a diagnostic composition intended to collect proteins from a target site of a subject, in particular a tumor and its microenvironment, usable to phenotype the target site.

Another object of the invention relates to a method for collecting proteins from a target site (allowing in particular the phenotyping of said target site) in a subject or patient, comprising a) administering thermosensitive liposomes to the patient suffering from the disorder or a composition such as herein described comprising such thermosensitive liposomes b) heating the thermosensitive liposomes at Tm or above Tm in order to allow the release of nanoparticles on the target site and their subsequent interaction with said target site, and c) subsequently collecting the nanoparticles covered with the proteins of said target site.

The previous method can further comprise a step of heating the thermosensitive liposomes at Tm or above Tm in order to allow the release of nanoparticles in the blood and a step of collecting the nanoparticles covered with blood proteins in order to compare blood proteins to proteins from the target site.

This approach constitutes an advantageous non-invasive technique when compared to classical biopsies.

The herein-described thermosensitive liposomes are a diagnostic tool usable in personalized therapy as they can provide information regarding the cancer stage of a particular patient, and may help the oncologist to select the most appropriate treatment for this patient or follow the efficiency of a particular treatment.

The herein-described thermosensitive liposomes can further provide information to assess a tumor response to a particular therapy and predict the clinical outcome (Progression-Free Survival) of the patient.

For this specific application any nanoparticles as described above may be used. Nanoparticles are preferentially made of a magnetic core as defined previously (e.g., $Fe_2O_3$ or $Fe_3O_4$).

For phenotyping the tumor, the use of nanoparticles comprising a coating together with a coupling group is preferred. Such a coupling group can advantageously be selected from succinimidyl ester, maleimide and any mixture thereof. This group will create a covalent link with amino and carboxylic groups usually present on proteins.

In a particular embodiment, the thermosensitive liposomes herein described are able to vehicle nanoparticles comprising a coating together with a coupling group in blood circulation while avoiding recognition by the reticuloendothelial system (RES).

Nanoparticles, released from the thermosensitive liposomes at Tm or above Tm, will interact with proteins of the target site. The nanoparticles covered with a population of said proteins can be collected in urine. The urine sample may be subsequently treated in order to concentrate nanoparticles before analysis of the protein population using, for example, mass spectrometry after enzymatic digestion of the proteins and analyses of peptidic fragments.

Magnetic nanoparticles can otherwise be collected from the target site using, for example, a magnetic collector.

Another object of the invention is a therapeutic or diagnostic composition comprising thermosensitive liposomes such as defined hereinabove and/or which can be obtained by the methods herein described, preferably together with a pharmaceutically acceptable excipient, vehicle or carrier.

The diagnostic composition may be combined with the pharmaceutical composition or assimilated to the pharmaceutical composition, in particular when the diagnosis and the treatment are performed simultaneously. In the latter situation, the same nanoparticles are generally used as a therapeutic and a diagnostic agent.

The compositions can be in the form of a liquid (particles in suspension), gel, paste, and the like. Preferred compositions are in the form of an injectable formulation, preferably in a liquid form.

The excipient, vehicle or carrier which is employed can be any classical support for this type of application, such as saline, isotonic, sterile, or buffered solutions, and the like. Compositions can also comprise stabilizers, sweeteners, surfactants, and the like. Compositions can be formulated for example in ampoules, bottles, and flasks, by using known techniques of pharmaceutical formulation.

The concentration of nanoparticles in a composition of the invention will be easily adjusted by the skilled person depending, in particular, on the intended use, the patient subject, the nature of the target cells and the selected route of administration.

The pharmaceutical composition can further comprise an additional therapeutic compound (distinct from a nanoparticle or of a population of nanoparticles as herein described) also intended to treat a disease, for example a cancer. This additional therapeutic compound can be encapsulated in the liposome together with nanoparticles.

The present disclosure further provides kits comprising any one or more of the herein-described thermosensitive liposomes or compositions. Typically, the kit comprises at least one thermosensitive liposome or population of thermosensitive liposomes according to the present invention. Generally, the kit also comprises one or more containers filled with one or more of the ingredients of the pharmaceutical or diagnostic compositions of the invention. Associated with such container(s), a labeling notice providing instructions for using the products can be provided for using the thermosensitive liposome, population of thermosensitive liposomes, or compositions according to the present methods.

Other aspects and advantages of the invention will become apparent in the following examples, which are given for purposes of illustration and not by way of limitation.

EXPERIMENTAL SECTION

Example 1: Preparation of 5 nm-Sized Nanoparticles

Iron oxide nanoparticles with a size distribution centered on 5 nm are synthesized by coprecipitation of ferrous and ferric ions adapted from U.S. Pat. No. 4,329,241 and Bacri et al., J. Magn. Magn. Mat., 1986, 62:36-46).

Briefly, the reacting medium, with controlled ionic strength, consists of a solution of sodium nitrate 3M maintained at pH 12. A 3M sodium nitrate solution of ferrous and ferric ions in a molar ratio Fe(III)/Fe(II) equal 2 is prepared and slowly added to the reacting medium under mixing. It rapidly turns black. The whole solution is then aged during one night at ambient temperature under mixing.

Ferrite nanoparticles are then sedimented on a magnet and the supernatant is removed in order to eliminate the reacting medium. Then peptization (acidification) and oxidation of the nanoparticles' surface is performed by diluting the pellet in a solution of nitric acid $HNO_3$ 2M at room temperature under vigorous mixing.

Oxidation of the nanoparticles' core is performed by incubation of the pellet in a solution of ferric nitrate at elevated temperature (>90° C.) under vigorous mixing.

The nanoparticles are then washed by centrifugation.

The pellet is finally diluted in acidic water in order to reach a concentration of 150 g/L in iron oxide. The solution is homogenized by sonication and pH is then adjusted to pH 2.

The morphology (size and shape) of nanoparticles was observed by Transmission Electron Microscopy (FIG. 2A). The crystalline structure of iron oxide nanoparticles was confirmed by X-ray diffraction analysis.

Example 2: Preparation of 30 nm-Sized Iron Oxide Nanoparticles

Iron oxide nanoparticles with a size distribution centered on 30 nm were synthesized by precipitation of ferrous ions followed by oxidation of the precipitate.

The aqueous reacting medium was maintained at pH 8 under continuous bubbling of nitrogen flow. A solution of ferrous chloride and a solution of sodium hydroxide were prepared and added simultaneously to the reacting medium. The solution turned green and highly turbid ("milky").

Oxidation step was performed by adding $H_2O_2$ solution. The solution turned black, indicating the formation of the ferrite material. The nitrogen flow was removed after complete addition of $H_2O_2$. The ferrite nanoparticles were then aged during 2 h under stirring.

The ferrite nanoparticles were sedimented on a magnet to remove the supernatant. Peptization of the nanoparticles' surface with perchloric acid ($HClO_4$) was performed by diluting the pellet in a solution of $HClO_4$ 1M.

Finally, peptized nanoparticles were suspended in distilled water in order to obtain a magnetic fluid at 180 g/L and pH 2.

Size and shape of the as-obtained iron oxide nanoparticles were observed by Transmission Electron Microscopy (FIG. 2B). The crystalline structure of iron oxide nanoparticles was confirmed by X-ray diffraction analysis.

Example 3: Surface Treatment of Nanoparticles 3.1 Functionalization of Nanoparticles with Sodium Hexametaphosphate (HMP)

Suspension of sodium hexametaphosphate is added to the suspension of iron oxide nanoparticles from example 1 (the amount of sodium hexametaphosphate added being below LD50/5) and the pH of the suspension is adjusted to a pH comprised between 6 and 8.

Electronic surface charge (←−20 mV) is determined by zeta potential measurements on a Zetasizer NanoZS (Malvern Instruments), using a 633 nm HeNe laser, performed on nanoparticle suspensions with concentrations varying between 0.2 and 2 g/L, the nanoparticles being suspended in an aqueous medium at a pH comprised between 6 and 8.

3.2 Functionalization of Nanoparticles with Silica

A first silica impregnation is performed by addition of sodium silicate in particle solution (7804, for 1 g particles from example 2 in 240 mL distilled water). Remaining sodium silicate is removed by a centrifugation against water. 125 mg particles are dispersed in water/ethanol (¼) solution containing 0.6 mmoles of tetraorthosilicate. Silica precursor hydrolyzation and condensation are enhanced by addition of ammonium solution in the bulk. Solution is incubated overnight before washing particles by centrifugation in distilled water. Coated particles are kept in water (pH is adjusted to about 7.4).

Electronic surface charge (←−20 mV) is determined by zeta potential measurements on a Zetasizer NanoZS (Malvern Instruments), using a 633 nm HeNe laser, performed on nanoparticle suspensions with concentrations varying between 0.2 and 2 g/L, the nanoparticles being suspended in an aqueous medium at a pH comprised between 6 and 8.

3.3 Functionalization of Nanoparticles with 2-[methoxy (polyethyleneoxy)propyl]trimethoxysilane; 90% 6-9 PE-Units (PEO-Silane)

PEO-silane is covalently grafted onto the iron oxide nanoparticles' surface (nanoparticles from example 1) thanks to a hydrolysis-condensation process catalyzed in acidic medium.

Suspension of PEO-silane is added to the suspension of iron oxide nanoparticles from example 1. Typically a volume of 2464, of a solution of PEO-silane (92% wt) is added to 2 mL of nanoparticle solution at 75 g/L in iron oxide. The pH of the solution is then adjusted to a pH comprised between 6 and 8.

Electronic surface charge (+8 mV) is determined by zeta potential measurements on a Zetasizer NanoZS (Malvern Instruments), using a 633 nm HeNe laser, performed on nanoparticle suspensions with concentrations varying between 0.2 and 2 g/L, the nanoparticles being suspended in an aqueous medium at a pH comprised between 6 and 8.

Example 4: Preparation of Liposomes Containing Nanoparticles 4.1 "Thermosensitive Liposomes" (TSL) Containing Nanoparticles the Charge of which is Below −20 mV:

The nanoparticle-containing liposomes are prepared using the lipidic film re-hydration method (Bangham et al., J. Mol. Biol., 1965, 13:238-252; Martina et al., J. Am. Chem. Soc., 2005, 127:10676-10685):

a) Lipids are solubilized in chloroform. Chloroform is finally evaporated under a nitrogen flow. Re-hydration of the lipidic film is performed at 55° C. with 2 mL of the iron oxide solution described in Example 3.1, so that the lipidic concentration is 50 mM.

Figure 3:
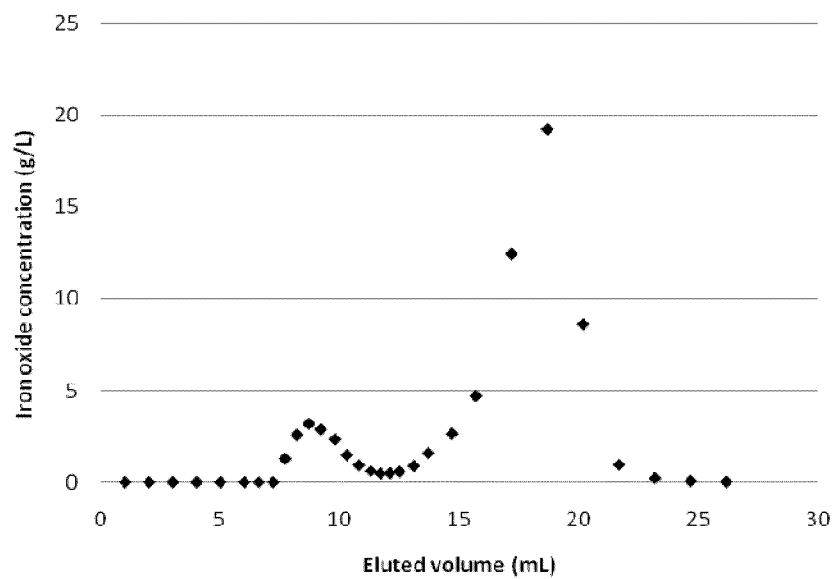
FIG. 3: Typical elution profile obtained for iron oxide-containing liposomes.

The following lipidic composition was used: dipalmitoylphosphatidylcholine (DPPC), hydrogenated soybean phophatidylcholine (HSPC), cholesterol (Chol) and pegylated distearylphosphatidylethanolamine (DSPE-PEG2000) in the molar ratio 100:33:27:7 (DPPC:HSPC:Chol:DSPE-PEG2000).

b) Freeze-thaw cycles are then performed 20 times, by successively plunging the sample into liquid nitrogen and into a water bath regulated at 55° C.

c) A thermobarrel extruder (LIPEX™ Extruder, Northern Lipids) was used to calibrate the size of the nanoparticle-containing liposomes under controlled temperature and pressure. In all cases, extrusion was performed at 55° C., under a pressure ranging from 2 to 20 bars.

d) Separation of non-encapsulated particles is performed by size exclusion chromatography on a Sephacryl S1000 filtration gel.

e) Elution profile is determined by quantification of magnetic nanoparticles by UV-visible spectroscopy (Cary 100 Varian spectrometer) via a ferrous ion/phenanthroline colorimetric reaction adapted from Che et al., Journal of Chromatography B, 1995, 669:45-51 and Nigo et al., Talanta, 1981, 28:669-674. Liposome-containing fractions are collected (FIG. 3, first peak). The concentration of iron oxide in liposomes ranges from 1 to 2.5 g/L.

Such a composition has a Tm of 43° C.

4.2 "Non-Thermosensitive Liposomes" (NTSL) Containing Nanoparticles the Charge of which is Below −20 mV The previously described procedure was followed except that in step a) the following lipidic composition was used: hydrogenated soybean phosphatidylcholine (HSPC), cholesterol (Chol) and pegylated distearylphosphatidylethanolamine (DSPE-PEG2000) in the molar ratio 100:65:7 (HSPC:Chol:DSPE-PEG2000).

In steps a), b) and c), re-hydration of the lipidic film, thaw cycles and extrusion process are performed at 62° C.

4.3 "Thermosensitive Liposomes" (TSL) Containing Nanoparticles the Charge of which is Below 15 mV The previously described procedure of example 4.1 was followed except that nanoparticles from example 3.3 were used.

Example 5: Nanoparticle Release

In order to visualize the release of nanoparticles entrapped in liposomes, 30 μL of the solutions of nanoparticles-containing liposomes as prepared in Examples 4.1 and 4.2 were heated in a water bath.

For cryoTEM observations, 5 μL of each solution was then deposited on a holey carbon coated copper grid; the excess was blotted with a filter paper, and the grid was plunged into a liquid ethane bath cooled with liquid nitrogen. Samples were maintained and observed at a temperature of approximately −170° C.

FIGS. 4A and 4B show spherical, 230 nm-sized "non-thermosensitive" liposomes (NTSL) containing iron oxide nanoparticles, prior and after heating at 60° C. in a water bath.

FIGS. 4C and 4D show spherical, 200 nm-sized "thermosensitive" liposomes (TSL) containing iron oxide nanoparticles, prior and after heating in a water bath at 43° C. ($T_m$).

FIG. 4E shows spherical, 200 nm-sized "thermosensitive" liposomes (TSL) containing iron oxide nanoparticles, after heating in a water bath at 48° C. (above $T_m$).

FIG. 4F shows thermosensitive liposomes loaded with iron oxide nanoparticles (example 4.3) aged at room temperature.

FIG. 4G shows thermosensitive liposomes loaded with iron oxide nanoparticles (example 4.3) aged at 43° C. (Tm).

Concerning "non-thermosensitive" liposomes (NTSL), intact, 230 nm-sized liposomes are seen both before and after heating (FIGS. 4A and 4B).

Concerning "thermosensitive" liposomes (TSL), intact, 200 nm-sized liposomes are seen before heating (FIG. 4C).

On the contrary, after heating at $T_r$=43° C. (FIG. 4D) and $T_r$=48° C. (FIG. 4E), 200 nm-sized liposomes present a modified shape (FIG. 4E, white arrow) and disruption of the bilayer; some fragments of lipidic bilayer can also be seen. Some pictures show vesicles for which intact lipidic membranes are not observed anymore after heating and iron oxide nanoparticles are localized around the lipidic vesicles (FIG. 4D). Free iron oxide nanoparticles are frequently observed on the grid. The release of nanoparticles is demonstrated for a temperature $T_r$=$T_m$=43° C. or for a temperature above $T_m$ (48° C.). Interactions between charged nanoparticles and the lipidic bilayer (FIG. 4E, black arrow) could explain this surprising result.

The invention claimed is:

1. A thermosensitive liposome comprising a thermosensitive lipidic membrane encapsulating nanoparticles, said thermosensitive lipidic membrane having a main phase transition temperature ($T_m$) between 39° C. and 55° C. and releasing said nanoparticles when heated to gel-to-liquid crystalline phase transition temperature (Tm) of between 39° C. and 55° C., the nanoparticles i) comprising an inorganic core the largest dimension of which is less than about 100 nm, and ii) being fully coated with an agent responsible for the presence of an electrostatic charge below −20 mV or above +20 mV at the surface of the nanoparticle, the electrostatic charge being determined by zeta potential measurements in an aqueous medium between pH 6 and 8, for a concentration of nanoparticles in suspension in the aqueous medium varying between 0.2 and 8 g/L.

2. The thermosensitive liposome according to claim 1, wherein the thermosensitive lipidic membrane comprises at least a phosphatidylcholine.

3. The thermosensitive liposome according to claim 2, wherein the thermosensitive lipidic membrane further comprises cholesterol.

4. The thermosensitive liposome according to claim 1, wherein the thermosensitive lipidic membrane comprises dipalmitoylphosphatidylcholine, hydrogenated soybean phosphatidylcholine, cholesterol and distearylphosphatidylethanolamine-methoxypolyethyleneglycol.

5. The thermosensitive liposome according to claim 2, wherein the thermosensitive lipidic membrane comprises dipalmitoylphosphatidylcholine, distearylphosphatidylethanolamine-methoxypolyethyleneglycol and either monopalmitoylphosphatidylcholine or monostearylphosphatidylcholine.

6. The thermosensitive liposome according to claim 1, wherein the agent responsible for the presence of the electrostatic charge at the surface of the nanoparticle is an organic molecule having two groups, R and X, R being selected from an amine, a phosphate and a carboxylate and X being selected from a carboxylate, a silane, a phosphonic, a phosphoric, a phosphate, and a thiol.

7. The thermosensitive liposome according to claim 6, wherein the nanoparticle further comprises a coupling group selected from a succinimidyl ester and a maleimide group.

8. The thermosensitive liposome according to claim 1, wherein the nanoparticles further comprise a targeting group selected from a peptide, an oligopeptide, a polypeptide, a protein, a nucleic acid, a hormone, a vitamin, an enzyme, a ligand of a tumor antigen, a hormone receptor, a cytokine receptor and a growth factor receptor.

9. The thermosensitive liposome according to claim 1, wherein the largest size of the liposome is between 50 and 500 nm.

10. The thermosensitive liposome according to claim 1, wherein the largest size of the liposome is between 50 and 250 nm.

11. The thermosensitive liposome according to claim 1, wherein Tm is between 39° C. and 45° C.

12. The thermosensitive liposome according to claim 1, wherein, when nanoparticles are used as a therapeutic agent, the largest dimension of the core of each nanoparticle is between 5 nm and 100 nm.

13. The thermosensitive liposome according to claim 1, wherein, when nanoparticles are used as a therapeutic agent, the largest dimension of the core of each nanoparticle is between 10 nm and 50 nm.

14. The thermosensitive liposome according to claim 1, wherein, when nanoparticles are used as a diagnostic agent, the largest dimension of the core of each nanoparticle is between 2 and 10 nm.

15. The thermosensitive liposome according to claim 1, wherein the thermosensitive lipidic membrane comprises dipalmitoylphosphatidylcholine (DPPC), hydrogenated soybean phosphatidylcholine (HSPC), cholesterol and distearylphosphatidylethanolamine (DSPE)-methoxypolyethylene glycol (PEG) in a molar ratio of 100:50:30:6 or 100:33:27:7.

16. A therapeutic composition comprising a thermosensitive liposome according to claim 1 and a pharmaceutically acceptable carrier.

17. A diagnostic composition comprising a thermosensitive liposome according to claim 1 and a pharmaceutically acceptable carrier.

* * * * *

UNITED STATES PATENT AND TRADEMARK OFFICE
CERTIFICATE OF CORRECTION

PATENT NO. : 9,956,175 B2
APPLICATION NO. : 13/981757
DATED : May 1, 2018
INVENTOR(S) : Agnès Pottier et al.

Page 1 of 1

It is certified that error appears in the above-identified patent and that said Letters Patent is hereby corrected as shown below:

In the Specification

Column 21,
Line 26, "(7804," should read --(780μL--.
Line 52, "2464," should read --246μL--.

Signed and Sealed this
Twentieth Day of August, 2019

Andrei Iancu
*Director of the United States Patent and Trademark Office*